(12) United States Patent
Friedrich

(10) Patent No.: US 6,617,411 B1
(45) Date of Patent: Sep. 9, 2003

(54) POLYCONDENSATION OF ORGANIC SILICON COMPOUNDS

(75) Inventor: Thomas Friedrich, Darmstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/717,035

(22) Filed: Nov. 22, 2000

(30) Foreign Application Priority Data

Sep. 18, 2000 (DE) ......................................... 100 46 039

(51) Int. Cl.$^7$ .............................................. C08G 77/08
(52) U.S. Cl. ........................................... 528/21; 528/12
(58) Field of Search ..................................... 528/21, 12

(56) References Cited

U.S. PATENT DOCUMENTS

| | | | |
|---|---|---|---|
| 5,200,334 A | * 4/1993 | Dunn et al. | 435/182 |
| 6,080,402 A | * 6/2000 | Reetz et al. | 424/94.6 |
| 6,303,290 B1 | * 10/2001 | Liu et al. | 435/4 |

FOREIGN PATENT DOCUMENTS

WO    WO 00/35993    6/2000

OTHER PUBLICATIONS

Shuyi Qiu et al., Chemical Abstracts, Huanan Ligong Daxue Xuebao, Ziran Kexueban, AN 1998:125965, DN 128:229390, vol. 25, No. 9, 1 page, "Lipase–Catalyzed Bioconversion of Organosilyl Alcohol in Microaqueous Phase", 1997.

A. F. Holleman, et al., Lehrbuch der Anorganischen Chemie, Walter de Gruyter Verlag, 91st–100th edition, pp. 757–764, "2.6 Sauerstoffsaeren des Siliciums. Silicate und Silicone".

A. F. Holleman, et al., Lehrbuch der Anorganischen Chemie, Walter de Gruyter Verlag, 91st–100th edition, pp. 786–788, "2.6.5 Silicone".

J. N. Cha, et al., Proc. Natl. Acad. Sci., vol. 96, pp. 361–365, "Silicatein Filaments and Subunits From a Marine Sponge Direct the Polymerization of Silica and Silicones In Vitro", Jan. 1999.

L. G. J. Frenken, et al., Applied and Environmental Microbiology, vol. 58, No. 12, pp. 3787–3791, "Cloning of the *Pseudomonas glumae* Lipase Gene and Determination of the Active Site Residues", Dec. 1992.

S. JØrgensen, et al., Journal of Bacteriology, vol. 173, No. 2, pp. 559–567, "Cloning, Sequence, and Expression of a Lipase Gene From Pseudomonas cepacia: Lipase Production in Heterologous Hosts Requires Two *Pseudomonas* Genes", Jan. 1991.

S. Wohlfarth, et al., Journal of General Microbiology, vol. 138, pp. 1325–1335, "Molecular Genetics of the Extracellular Lipase of *Pseudomonas aeruginosa* PAO1", 1992.

* cited by examiner

Primary Examiner—Margaret G. Moore
(74) Attorney, Agent, or Firm—Oblon, Spivak, McClelland, Maier & Neustadt, P.C.

(57) ABSTRACT

A process is described for the polycondensation of organic silicon compounds at from pH 6 to 8 in the presence of a lipase which is, where appropriate, immobilized on a carrier composed of polymer materials. Suitable organic silicon compounds capable of polycondensation are $(RO)(R^1O)(R^2O)(R^3O)Si$, $(RO)(R^1O)(R^2O)SiR^3$, $(RO)(R^1O)Si(R^2)(R^3)$ and $(RO) SiR^1R^2R^3$, where R, $R^1$, $R^2$ and $R^3$ are independently of one another $C_1$- to $C_{10}$-alkyl, $C_3$- to $C_{10}$-cycloalkyl, $C_4$- to $C_{20}$-alkylcycloalkyl, aryl, $C_6$- to $C_{16}$-alkylaryl, the alkyl groups being linear or branched. It is advantageous and possible to obtain the lipase on a large scale relatively simply by fermentation processes. Preference is given to employing lipases from Pseudomonas species.

20 Claims, 3 Drawing Sheets

POLYCONDENSATION OF ORGANIC SILICON COMPOUNDS

The invention relates to a process for polycondensation of organic silicon compounds in the presence of an enzyme.

Silicones and silicates are of industrial-scale importance. Silicates are employed, for example, as phase material in chromatography. There are numerous processes for their preparation. Processes leading to amorphous silicates, for example, start from orthosilicic acid which is condensed in aqueous solution with acid or base catalysis (A. F. Holleman, E. Wiberg, Lehrbuch der Anorganischen Chemie [Textbook of Inorganic Chemistry], Walter de Gruyter Verlag, Berlin N.Y. 1985, 91st–100th edition, pp. 757–764). Silicones can be prepared by condensation of silanols, silanediols and silanetriols (A. F. Holleman, E. Wiberg, Lehrbuch der Anorganischen Chemie, Walter de Gruyter Verlag, Berlin N.Y. 1983, 91st–100th edition, pp.786–788). In novel processes developed in the last few years it is possible to condense organic silicon compounds under mild conditions. Enzymes are employed as catalysts. The reactions can be carried out at from pH 6 to pH 8. In 1998 a suitable enzyme has been isolated for the first time from a marine sponge, as described in J. N. Cha, K. Shimizu, Y. Zhou, S. C. Christiansen, B. F. Chmelka, G. D. Stucky, D. E. Morse, Proc. Natl. Acad. Sci. USA 1999, 96, 361–365. The enzyme is composed of three subunits, the so-called silicateins. Extracting the enzyme is relatively costly. Besides polycondensation in buffer solution, the organic silicon compounds $(EtO)_4Si$ and $(EtO)_3SiPh$ have been converted directly using air-dried enzyme. Moreover, WO 00/35993 describes employing synthetic homopolymers composed of cysteine and block polypeptides composed of lysine and cysteine for polycondensation of silicon alkoxides, metal alkoxides and derivatives thereof into silicates, polysiloxanes and polymetaloxanes.

It is an object of the present invention to provide a further process for the polycondensation of organic silicon compounds, which can be carried out at from pH 6 to 8, and to find a suitable catalyst for this reaction.

The object is achieved by starting from the known process for the polycondensation of organic silicon compounds in solution at from pH 6 to 8 in the presence of an enzyme. The process of the invention comprises employing a lipase as the enzyme. This is surprising because lipases possess no structural similarity to previously employed enzymes such as silicateins.

In general, all lipases are suitable for the process of the invention; preferred are lipases from *Pseudomonas* species, particularly preferred are *Burkholderia plantarii* lipase (EC 3.1.1.3; SWISS-PROT: Q05489; L. G. J. Frenken, M. R. Egmond, A. M. Batenburg, J. W. Bos, C. Visser, C. T. Verrips, Appl. Environ. Microbiol. 1992, 58, 3787–3791), *Burkholderia cepacia* lipase A (EC 3.1.1.3; SWISS-PROT: P22088; S. Joergensen, K. W. Skov, B. Diderichsen, J. Bacteriol. 1991, 173, 559–567) and *Pseudomonas aeruginosa* lipase A (EC 3.1.1.3; SWISS-PROT: P26876; S. Wohlfarth, C. Hoesche, C. Strunk, U. K. Winkler, J. Gen. Microbiol. 1992, 138, 1325–1335), and very particularly preferred is *Burkholderia plantarii* lipase.

It is advantageous and possible to produce lipases on a large scale by fermentation processes. A bacterial lipase, for example, can be produced by fermentation of bacteria secreting the desired lipase in a nutrient medium containing yeast extract, soybean oil and usual additives such as mineral salts and trace elements and, where appropriate, buffer substances. After completion of the fermentation, the lipase may be removed from the bacterial cells and cell constituents, for example by centrifugation or filtration, and be purified by processes such as ion exchange chromatography, molecular sieve chromatography, hydrophobic chromatography and precipitation methods. Purification of the lipase is not necessary if the lipase is immobilized on carriers such as polyolefin particles and polyurethane foams after removal from the bacterial cells and cell constituents. Immobilization means that enzymes from anhydrous or aqueous solutions are bonded to, in particular, nonpolar matrices having a large surface area permanently and with retention of the catalytic activity. Immobilization reduces the loss in lipase during working-up and allows polycondensation of organic silicon compounds to be carried out even in organic solvents in which free lipase is insoluble. In addition, the polycondensation products may grow on the carrier, thus resulting in possible novel applications for producing components in microelectronics.

When employing polyurethane foams as carriers, the enzymes are immobilized on the carrier by reacting the enzymes with reactive groups on the surface of the polyurethane foam. The enzymes are covalently bonded to the surface. Such reactive groups may be NCO groups, epoxide groups, $CO_2H$ groups and/or phenolic OH groups which, where appropriate, were attached to the polyurethane foam surface only after polymerization.

When employing polyolefin particles as carriers, the bond between enzyme and carrier is based inter alia on hydrophobic interactions. Suitable polyolefins are homopolymers and copolymers composed of unsubstituted or substituted olefins such as ethylene, propylene, butadiene, butene, octene or styrene; preference is given to employing polypropylene as a carrier.

Lipases which are present in solutions obtained by fermentation of bacteria, fermenter solutions, are usually immobilized on polyolefin particles as follows: bacterial cells and cell constituents are removed from the fermenter solution, for example by centrifugation. The remaining solution is diluted with water and the polyolefin particles are contacted with this solution which contains the lipase. The contacting takes place, for example, by adding the polyolefin particles to the lipase-containing solution. When the lipase-containing solution is contacted with the polyolefin particles, the lipase is adsorbed onto the polyolefin particles. The polyolefin particles have a very high selectivity for lipases. Only the lipase and, where appropriate, its fragments are predominantly adsorbed onto the polyolefin particles. The proportion of other proteins adsorbed from the lipase-containing solution onto the polyolefin particles is normally below 2% by weight. The adsorption is thus also a step to purify the lipase from the other proteins and enzymes in the lipase-containing solution.

The particle size and the void fraction of the polyolefin particles is not critical. Preferred polyolefin particles have a particle size of from 100 $\mu$m to 2000 $\mu$m, particularly preferred polyolefin particles have a particle size of from 200 $\mu$m to 1000 $\mu$m. The void fraction of the polyolefin particles is preferably 40% to 80%, particularly preferably 60% to 70%, very particularly preferably 65%. The pore size of the polyolefin particles is preferably 0.01 $\mu$m to 1 $\mu$m, particularly preferably 0.05 to 0.5 $\mu$m.

In one embodiment of the invention, propylene carriers Accurel® from Akzo are employed as carriers having particle sizes of <400 $\mu$m (Accurel 1004), of from 400 to 1000 $\mu$m (Accurel 1001) and of >1000 $\mu$m (in pellet form); preference is given to employing Accurel 1004 and Accurel 1001.

The optimal duration of lipase immobilization on polyolefin particles depends on the lipase and on the type of polyolefin particles and can be determined by routine tests. Normally, the immobilization lasts for 10 min to 24 h, preferably 4 to 24 h, particularly preferably 4 to 6 h.

Normally, the immobilization takes place at from pH 4.0 to 8.8, preferably from 4.5 to 7.8, particularly preferably from 4.5 to 6.0.

The ionic strength, which may be determined by conductivity measurement, should normally be <0.5 M, preferably <0.3 M.

Immobilizing the lipase on the polyolefin particles is also called loading the polyolefin particles with the lipase. A preferred loading at which a maximum amount of lipase is adsorbed and a minimum amount of lipase remains in the solution is dependent on the type of polyolefin and can be determined by routine tests. Normally, the amount of lipase immobilized on polyolefin particles is from 0.1 to 50 mg of lipase per g of carrier, preferably from 0.5 to 20 mg of lipase per g of carrier, particularly preferably from 2 to 6 mg of lipase per g of carrier. In a very particularly preferred embodiment of the invention said amount is 4.2 mg of lipase per g of carrier.

It is advantageous for the immobilized lipase to be purified, before use as catalyst, from unadsorbed material by washing with a suitable solvent such as water. The immobilized lipase is then, where appropriate, dried in air. The residual moisture is normally less than 4%.

The process described for immobilizing lipases on polyolefin particles may be carried out not only with lipases which are present in solutions obtained by fermentation but generally with lipases which are present in aqueous or organic solvents (for example in halogenated or nonhalogenated aliphatic and aromatic hydrocarbons) or in aqueous buffer solution. The process may also be carried out with lipases purified prior to the immobilization, but a purification is not necessary. Other processes known to the skilled worker may also be used for immobilizing lipases.

Immobilized lipase can be employed as a catalyst for polycondensation of organic silicon compounds in the same way as free lipase. In comparison with free lipase, immobilized lipase is characterized by increased stability and useful life on carrying out the reaction continuously and batchwise and by easy recovery of the catalytically active species in batchwise reactions.

Organic silicon compounds which are suitable for the process of the invention and capable of polycondensation are $(RO)(R^1O)(R^2O)(R^3O)Si$, where R, $R^1$, $R^2$ and $R^3$ may be independently of one another $C_1$- to $C_{10}$-alkyl, $C_3$- to $C_{10}$-cycloalkyl, $C_4$- to $C_{20}$-alkylcycloalkyl, aryl, $C_6$- to $C_{16}$-alkylaryl and the alkyl groups may be linear or branched.

$(RO)(R^1O)(R^2O)SiR^3$, where R, $R^1$, $R^2$ and $R^3$ may be independently of one another $C_1$- to $C_{10}$-alkyl, $C_3$- to $C_{10}$-cycloalkyl, $C_4$- to $C_{20}$-alkylcycloalkyl, aryl, $C_6$- to $C_{16}$-alkylaryl and the alkyl groups may be linear or branched.

$(RO)(R^1O)Si(R^2)(R^3)$, where R, $R^1$, $R^2$ and $R^3$ may be independently of one another $C_1$- to $C_{10}$-alkyl, $C_3$- to $C_{10}$-cycloalkyl, $C_4$- to $C_{20}$-alkylcycloalkyl, aryl, $C_6$- to $C_{16}$-alkylaryl and the alkyl groups may be linear or branched.

$(RO)SiR^1R^2R^3$ where R, $R^1$, $R^2$ and $R^3$ may be independently of one another $C_1$- to $C_{10}$-alkyl, $C_3$- to $C_{10}$-cycloalkyl, $C_4$- to $C_{20}$-alkylcycloalkyl, aryl, $C_6$- to $C_{16}$-alkylaryl and the alkyl groups may be linear or branched.

Preference is given to employing tetraalkoxysilanes $(RO)_4Si$ and trialkoxyarylsilanes $(R^1O)_3SiR^2$ with R, $R^1$=Me, Et, Pr, iPr, Bu and $R^2$=aryl. Reacting silanes with aryl groups has the advantage that aryl groups absorb UV light and that therefore such silanes are detectable by UV detectors.

When tetraalkoxysilanes and trialkoxyalkylsilanes are employed for polycondensation, then, depending on how the reaction is conducted, linear, branched and crosslinked silicates having hydroxy, alkoxy, alkyl, cycloalkyl, alkylcycloalkyl, aryl, and alkylaryl radicals on the surface are obtainable.

Polycondensation of dialkoxydialkylsilanes leads to silicones. When dialkoxydialkylsilanes and alkoxytrialkylsilanes are employed in the polycondensation of tetraalkoxysilanes, then these may serve as regulators and reduce the molar mass of the resulting oligosilicates and polysilicates.

When employing free or immobilized lipase, it is possible to employ as a solvent water or a buffer solution in which the lipase is readily soluble. The buffer solutions can be prepared by dissolving buffer substances in water. Suitable buffer substances are organic buffer substances known as Good's buffers. Preference is given to buffer substances having amino groups, particularly preferred is tris (hydroxymethyl)-aminomethane (called TRIS buffer). Further suitable buffer substances buffering in the pH range from 6.5 to 7.4 can be found in the standard reference books.

The ionic strength of the buffer solutions employed is normally at from 1 mM to 100 mM, preferably from 5 mM to 50 mM, particularly preferably from 10 mM to 20 mM. Ionic strengths higher than 100 mM may induce uncontrolled polycondensation of the organic silicon compounds. For example, phosphate buffer solutions such as $H_2PO_4^-$/$HPO_4^{2-}$ buffers which buffer around pH 7 may react at an ionic strength of over 100 mM with the organic silicon compounds employed.

Since the organic silicon compounds dissolve poorly in water or diluted aqueous buffer solutions, the reaction solution must be mixed well.

When employing immobilized lipase, it is also possible to employ organic solvents such as higher alcohols having up to 8 carbons, aliphatic and aromatic hydrocarbons and ethers. Examples are methyl tert-butyl ether, cyclohexane and cyclohexanol. Since the organic silicon compounds are more soluble in these solvents than in water, the reaction normally proceeds faster in organic solvents than in aqueous solution. The solution in organic solvents must still contain a residual amount of water which is at least equimolar to the alkoxy groups in the reaction mixture in order to facilitate hydrolysis of the alkoxy groups and thus polycondensation.

Polycondensation is normally carried out at from pH 6 to 8, preferably at from pH 6.5 to 7.4, particularly preferably at from pH 6.8 to 7.2.

In general it is possible to conduct the reaction at from 0 to 60° C., preferably from 10 to 40° C., particularly preferably from 20 to 30° C.

The reaction may be carried out at both atmospheric pressure and increased pressure of up to 2 bar, preferably however at atmospheric pressure.

The reaction normally lasts for 1 h to 24 h.

One embodiment of the invention comprises carrying out the reaction by adding the organic silicon compound to the lipase-containing solution with stirring. In a further embodiment of the invention the lipase-containing solution is added with stirring to the organic silicon compound. Addition of the reactants may take place both continuously and batchwise, preferably batchwise.

The organic silicon compound may be added both in pure form and dissolved in the abovementioned organic solvents.

When using free lipase in water and/or solutions containing buffer substances, the mixing of lipase-containing solution and organic silicon compound normally creates an emulsion. When immobilized lipase is employed, then a suspension is formed. The product in most cases results in the form of a precipitate.

The amount of lipase employed is stated in units [U] per ml of solvent. The lipase activity at 20 to 23° C. in aqueous solution is determined by the conversion of the substrate tributyrin (=glyceryl tris(butanoate)) which is cleaved into glycerol and butyric acid by the lipase. The butyric acid concentration can be determined by titration with NaOH (1 N). From this follows $$1U = \text{substrate conversion } [\mu mol] \frac{1}{\text{time [min]}}$$

There is no change in lipase activity between 15° C. and 30° C. For example, 8.3 mg of lipase have an activity of 250,000 units.

The ratio of the amount of free lipase stated in units per ml $H_2O$ to the amount of organic silicon compound stated in mol is normally from 200 to 5000 units per ml of $H_2O$ and 4 mmol of organic silicon compound and preferably from 400 to 2000 units per ml of $H_2O$ and 4 mmol of organic silicon compound.

The ratio of the amount of immobilized lipase stated in units to the amount of organic silicon compound stated in mol is from 100 to 20,000 units per 4 mmol of organic silicon compound, preferably from 100 to 10,000 units per 4 mmol of organic silicon compound, for example in 1 ml of $H_2O$ as a solvent.

When using free lipase, the working-up normally takes place by removing the organic-aqueous phase and, where appropriate, the organic phase from the product-containing precipitate, preferably by centrifugation. The precipitate is then dialyzed against an organic solvent. Suitable solvents are all water-miscible alcohols such as, for example, MeOH, EtOH, iPrOH and nPrOH. The use of EtOH is preferred.

The reaction product may also be removed by molecular sieve chromatography and—at sufficiently high molar masses—by centrifugation, or—for sufficiently hydrophobic reaction products—by extraction using a nonpolar solvent.

The lipase which is in the organic-aqueous phase may be recovered, for example by ultrafiltration and chromatography.

When using immobilized lipase, the silicates grow on the carrier. The reaction product can be removed by filtration from the solution in which the reaction took place.

The molar mass of the product is usually determined by gel permeation chromatography. It is, however, also possible to determine the molar mass by mass-spectrometric methods such as MALDI-MS (MALDI=matrix assisted laser desorption ionization) or ESI-MS (ESI=electrospray ionization).

The following examples illustrate the invention in more detail.

EXAMPLES

Example 1

Fermentation of *Burkholderia plantarii* Lipase 200 ml of a preculture containing 1 g $MgSO_4 \cdot 7H_2O$, 3.5 g $KH_2PO_4$, 3.5 g $K_2HPO_4$, 5.0 g $(NH_4)H_2PO_4$, 0.02 g, $CaCl_2 \cdot 2H_2$ and 10 g of yeast extract (Difco) per 1 l of water were sterilized in a 1 l shaking flask with 2 bottom baffles at 121° C. for 30 minutes, and usual additives (trace elements) were added.

The preculture was obtained by incubating the contents of two of these shaking flasks, that is 400 ml, with one ampoule of *Burkholderia plantarii* at 30° C. for 9 hours.

A medium containing 110 g of yeast extract (Difco), 38.5 g $K_2HPO_4$, 38.5 g $KH_2PO_4$, 55 g $(NH_4)H_2PO_4$, 11 g $MgSO_4 \cdot 7H_2O$, 0.22 g $CaCl_2 \cdot 2H_2O$ was diluted to 11 l with deionized water and sterilized at 121° C. for 30 min, and common additives (trace elements) were added. This medium was then introduced into a 14 l fermenter.

The fermentation was carried out at 30° C., pH 6.5 and 1000 revolutions per minute and passing in 11 l of $O_2$ per min for three days. Soybean oil was added continuously during fermentation. The rate of addition was calculated according to formula I. The preculture was added half an hour after the start of the reaction.

$$S=V*SF*(e^{(ST*t)}-1)/t \qquad \text{(formula I)}$$

S=amount metered [g/h]

V=fermentation volume [1],

SF=110 [g/lh],

ST=0.01 [1/h], t=time after start [h]

The organism secreted lipase into the surrounding medium. After the fermentation had finished and after cooling to 15° C., the solution was discharged. The lipase activity was 8900 U/ml and was increased to 10,500 U/ml by centrifugation.

Example 2

Immobilization

The fermenter solution obtained from the above-described fermentation was centrifuged in 1 l vessels in the swing-out centrifuge RC-3B at 5000 to 6000 revolutions per minute in order to remove the cells. The lipase concentration was then approx. 10,000 units per ml. 25 ml of this fermenter solution were diluted with 75 ml of water and incubated with 1 g of Accurel 1001. The final lipase concentration was 250,000 units per g Accurel 1001. 8.3 mg of lipase were immobilized on 1 g of Accurel. Using Accurel 1004 achieved the same result.

Example 3

Polycondensation of Organic Silicon Compounds in Presence of Free Lipase 25 ml of phenyltriethoxysilane, $Ph(EtO)_3Si$ (organic phase) were added to 25 ml of water containing 50,000 units of free *Burkholderia plantarii* lipase (aqueous phase) at room temperature and atmospheric pressure and mixed with vigorous stirring, an emulsion being generated and silicate forming in the organic phase in the form of a white precipitate. After 24 h the two phases were separated by centrifugation. The supernatant solution of the organic phase was removed and the remaining white precipitate dialyzed against 2 l of ethanol overnight. The exclusion volume of the dialysis membrane was 10,000 Da. After 24 h the sample was removed from the dialysis bag and an insoluble precipitate was removed by centrifugation. The precipitate was analyzed by GPC. Polystyrene was used as a calibration substance. The molar mass of the polymers of the generated polycondensation mixture ranged from 800 to 2400 Da. Accordingly, the prepared polymers are composed of 4 to 40 units.

Figure 1:
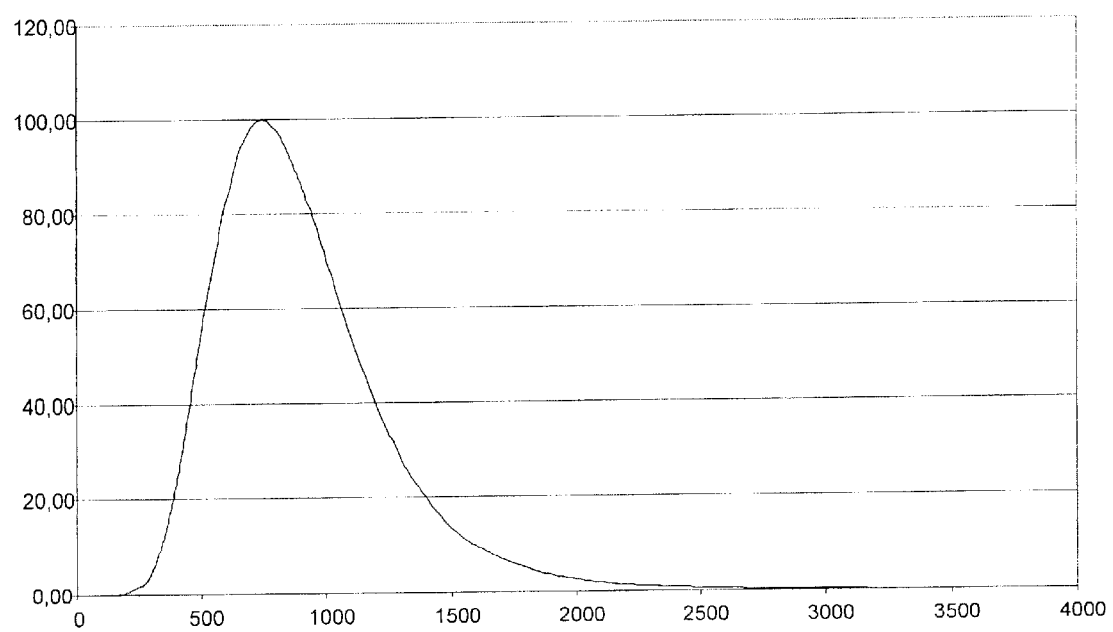
FIG. 1 shows the results of the molar mass determination from Example 3.

FIG. 1 shows the molar mass distribution of the polycondensation product from Example 3.

Example 4

Molar Mass Determination by Gel Permeation Chromatography

20 µl of a solution of 22 mg/ml (total sample from Example 3) were removed and filtered through Sartorius Minisart SRP 25 (0.2 µm). An S-628 column having an internal diameter of 4.6 mm and a length of 25 cm was employed for GPC. PL gel Mixed B [5 µm] was employed as separating material. Separation took place at a column temperature of 30° C. using THF as eluent and a flow rate of 0.3 ml/min. At this flow rate the column had 7000 theoretical plates. The exclusion limit for polystyrene was approx. $10^7$. An HP 1100 VWD UV photometer at 254 nm and an ELS-1000 evaporative light scattering detector were employed as detectors.

Narrow range polystyrene standards from Polymer Laboratories having molar masses of from 580 to $7.5 \cdot 10^6$ and hexylbenzene (molar mass of 162) were used for calibration. Elution zones outside this interval are estimated by extrapolation. The results can be found in FIG. 1.

Example 5

Figure 2:
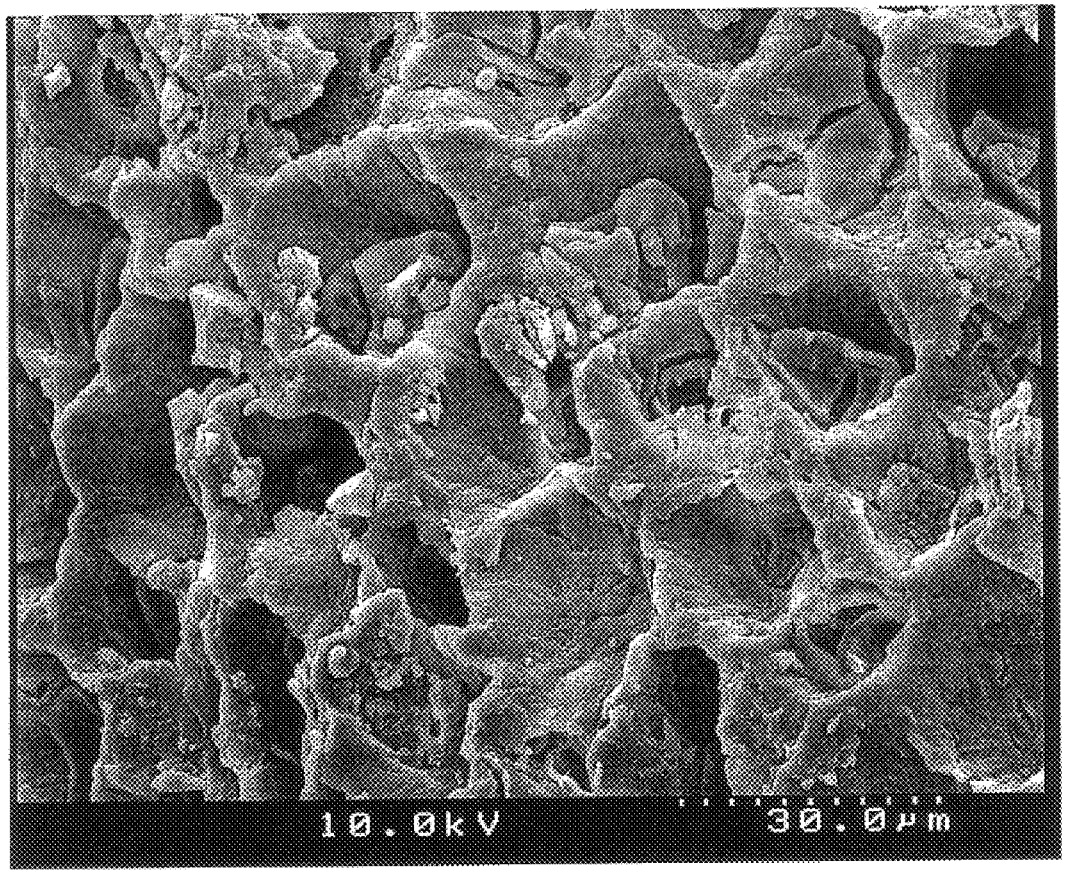
FIGS. 2 and 3 show crystalline growths formed by the polycondensation of organic silicon compounds in the presence of immobilized lipase.
Figure 3:
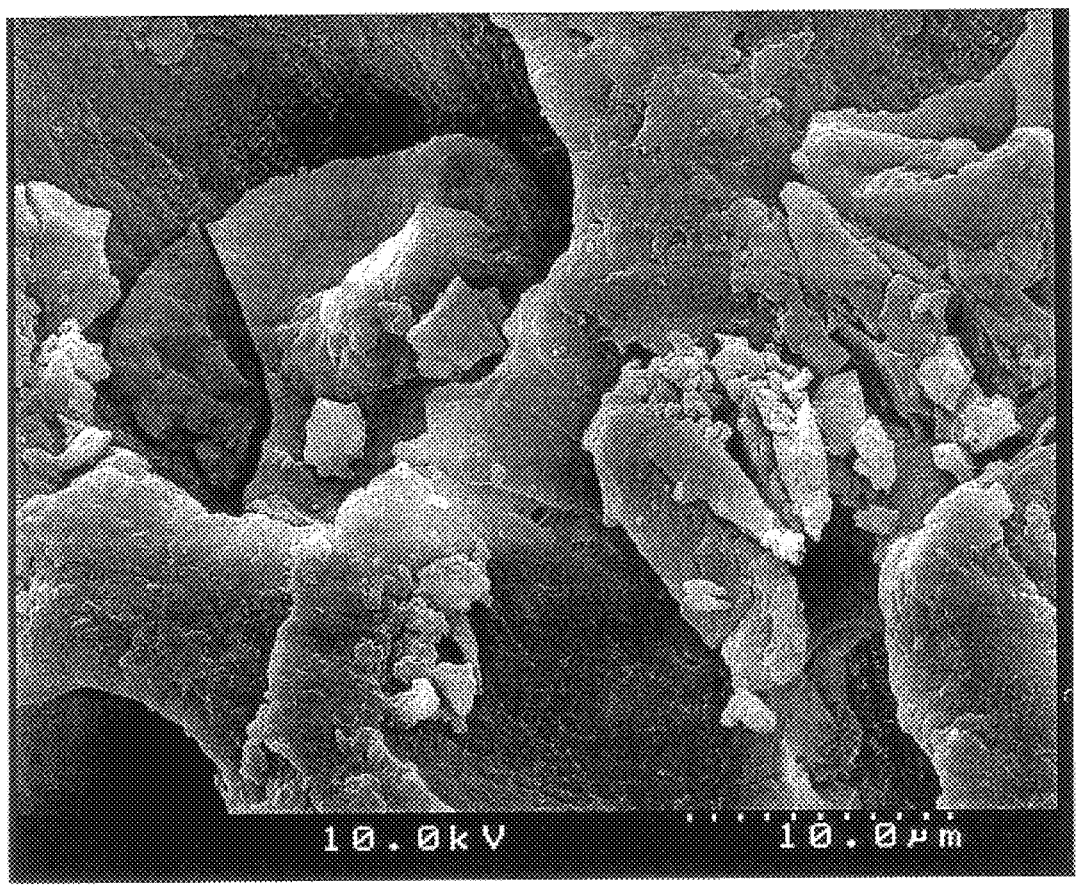

Polycondensation of Organic Silicon Compounds in Presence of Immobilized Lipase Tetrabutoxysilane was added to lipase immobilized on Accurel 1001 in aqueous solution and left at room temperature for 3 weeks. Crystalline growths formed on the carrier, specifically at sites occupied with lipase. FIGS. 2 and 3 clearly show the crystalline growths on the carrier.

I claim:
1. A process, comprising:
   polycondensing organic silicon compounds in a solution at a pH 6 to 8 in the presence of lipase enzyme as the sole polycondensation catalyst, thereby forming polycondensed organosilicon product.
2. The process as claimed in claim 1, wherein the lipase is immobilized on a carrier.
3. The process as claimed in claim 1, wherein the solution comprises water, a buffer solution, or a combination thereof.
4. The process as claimed in claim 2, wherein the solution comprises water, a buffer solution or an organic solvent.
5. The process as claimed in claim 2, wherein the carrier material comprises polypropylene, polystyrene, polyurethane foam or a combination thereof.
6. The process as claimed in claim 1, wherein the lipase is obtained from a species of *pseudomonas*.
7. The process as claimed in claim 1, which comprises removing the resulting polycondensation product from the lipase and purifying said product by dialysis.
8. The process as claimed in claim 1, wherein the organic silicon compound is selected from the group consisting of
   $(RO)(R^1O)(R^2O)(R^3O)Si$,
   $(RO)(R^1O)(R^2O)SiR^3$,
   $(RO)(R^1O)Si(R^2)(R^3)$ and
   $(RO)SiR^1R^2R^3$,
   where R, $R^1$, $R^2$ and $R^3$ are independently of one another $C_1$- to $C_{10}$-alkyl, $C_3$- to $C_{10}$-cycloalkyl, $C_4$- to $C_{20}$-alkylcycloalkyl, aryl, $C_6$- to $C_{16}$-alkylaryl, the alkyl groups being linear or branched.
9. The process as claimed in claim 1, wherein the lipase is a free lipase, and wherein the concentration of said free lipase ranges from 50 to 1250 units per mmol organic silicon compound.
10. The process as claimed in claim 1, wherein the lipase is an immobilized lipase, and wherein the solution comprises a small amount of water and an organic solvent selected from the group consisting of alcohols having up to 8 carbon atoms, an aliphatic hydrocarbon, an aromatic hydrocarbon and an ether.
11. The process as claimed in claim 1, wherein the polycondensation is conducted at a reaction temperature of 0 to 60° C.
12. The process as claimed in claim 11, wherein the reaction temperature ranges from 10 to 40° C.
13. The process as claimed in claim 1, wherein the polycondensation is conducted at a pH ranging from 6.5 to 7.4.
14. The process as claimed in claim 4, wherein the ionic strength of the buffer solution ranges from 1 mM to 100 mM.
15. A process for the polycondensation of organic silicon compounds in solution at a pH of 6 to 8 in the presence of an enzyme, wherein the enzyme is a lipase immobilized on a carrier and wherein the carrier material comprises at least one polymer selected from the group consisting of polypropylene, polystyrene and polyurethane foam.
16. The process as claimed in claim 15, wherein the solution comprises water or a buffer solution or an organic solvent or a combination thereof.
17. The process as claimed in claim 15, wherein the lipase is obtained from a species of *Pseudomonas*.
18. The process as claimed in claim 15, wherein the organic silicon compound is selected from the group consisting of
   $(RO)(R^1O)(R^2O)(R^3O)Si$,
   $(RO)(R^1O)(R^2O)SiR^3$,
   $(RO)(R^1O)Si(R^2)(R^3)$ and
   $(RO)SiR^1R^2R^3$,
   where R, $R^1$, $R^2$ and $R^3$ are independently of one another $C_1$- to $C_{10}$-alkyl, $C_3$- to $C_{10}$-cycloalkyl, $C_4$- to $C_{20}$-alkylcycloalkyl, aryl, $C_6$- to $C_{16}$-alkylaryl, the alkyl groups being linear or branched.
19. A process, comprising:
   polycondensing an organic silicon compound in solution at a pH of 6 to 8 in the presence of a lipase enzyme which catalyzes the polycondensation of said organic silicon compound to oligosilicone, oligosilicate, polysilicone or polysilicate product.
20. The process as claimed in claim 1, wherein the lipase is an immobilized lipase, and wherein the concentration of said immobilized lipase is from 25 to 5000 units per mmol organic silicon compound.

* * * * *